United States Patent
Dunnegan et al.

[11] Patent Number: 6,115,118
[45] Date of Patent: Sep. 5, 2000

[54] VEHICLE WINDSHIELD SCANNING SYSTEM

[75] Inventors: Garry Wayne Dunnegan, Wichita; Svetlozar Kovatchev, Derby, both of Kans.

[73] Assignee: Northstar Automotive Glass, Inc., Wichita, Kans.

[21] Appl. No.: 09/139,039

[22] Filed: Aug. 24, 1998

Related U.S. Application Data

[60] Provisional application No. 60/056,798, Aug. 25, 1997.

[51] Int. Cl.[7] .................................................. G01N 21/00
[52] U.S. Cl. ..................................... 356/239.1; 356/239.7; 348/128
[58] Field of Search .............................. 356/239.1, 239.2, 356/239.3, 239.7, 237.1, 429–431; 382/141, 142, 92; 348/92, 127, 129, 130, 88; 318/444, 483; 4/128

[56] References Cited

U.S. PATENT DOCUMENTS

| | | |
|---|---|---|
| H999 | 12/1991 | Merkel et al. ....................... 356/239.1 |
| 3,478,218 | 11/1969 | Wuellner et al. . |
| 4,492,477 | 1/1985 | Leser .................................... 356/239.1 |
| 4,725,139 | 2/1988 | Hack et al. .......................... 357/237.1 |
| 5,016,099 | 5/1991 | Bongardt et al. ....................... 358/106 |
| 5,602,648 | 2/1997 | Guering et al. ...................... 356/239.7 |
| 5,781,288 | 7/1998 | Asakura et al. .......................... 348/86 |

*Primary Examiner*—Hoa Q. Pham
*Attorney, Agent, or Firm*—Robert Blinn

[57] ABSTRACT

The windshield scanning system of the present invention includes a windshield scanner apparatus, a general purpose digital computer and an output device. The windshield scanner apparatus further includes a scanner which is adapted to crawl across a large portion of a windshield surface. The general purpose computer is programmed to receive scanner image data and analyze representative samples of the scanner image data to determine either the general surface condition of the windshield or the surface condition given by the worst sample. The computer output device is used to display the results of the analysis.

12 Claims, 5 Drawing Sheets

VEHICLE WINDSHIELD SCANNING SYSTEM

CROSS REFERENCES TO RELATED APPLICATIONS

This application claims the benefit of U.S. Provisional Patent Application Ser. No. 60/056,798 filed Aug. 25, 1997.

BACKGROUND OF THE INVENTION

1. Field of the Invention

The present invention relates to an apparatus and method for measuring the surface damage of a vehicle windshield using a digital imaging device.

2. Description of the Prior Art

Pitting and scratching of vehicle windshields has long been a problem that causes interference with operator vision and driving safety. "Direct Measurement of Windscreen Surface Wear and the Consequences of Road Safety" presented by A. Timmermann at the Conference on Vision in Vehicles, Nottingham, UK, 9-13 September 1985, presents an apparatus for measuring the light scatter of a localized beam of light as it passes through a vehicle windshield. It comprises a means for directing a parallel beam to a first light detector. A second light detector surrounding the first light detector at the focus point detects stray light that is diverted by the windshield surface damage. With Timmerman's device the ratio of stray light to direct light provides a measure of windshield damage. Timmermann's device yields exact measurements for localized windshield damage but requires expensive, specialized equipment. Further, significant time and effort is required in the use of Timmermann's device to assess the surface quality of a windshield.

Our investigations have shown that pitting varies widely across a windshield surface. Consequently, what is needed is a means for assessing pitting or surface damage over a large area of a windshield. We have found that a pattern of sample zones taken from a large area is an efficient and reliable means for assessing pitting or surface damage over a large area of a windshield. Further, we have found that values for pitting in pixels per square inch either on a worst case or on an average bases can be determined which correspond to a windshield having a unacceptable degree of surface damage or pitting.

Our investigations have also revealed that the peripheral glare produced by surface pitting in areas of the windshield opposite an operator's eye point can produce significant visual interference. A method and apparatus is needed to quickly assess windshield surface quality in windshield areas opposite the operator's eye point. Accordingly, what is needed is a method and apparatus for assessing windshield surface quality over large portions of a windshield surface and consequently what is also needed is a method and apparatus for assessing windshield surface quality in a windshield area opposite an operator's eye point.

SUMMARY OF THE INVENTION

The present invention satisfies these needs by providing a new apparatus and method for scanning a vehicle windshield and determining the amount of surface damage present in the surface of a vehicle windshield. The windshield scanning system of the present invention includes a windshield scanner apparatus, a general purpose digital computer, and an output device such as a screen or a printer. In a first embodiment, the windshield scanner apparatus and method further includes a scanner which is adapted to crawl across a large portion of a windshield surface. The general purpose digital computer is programmed to receive scanner image data and analyze representative samples of the scanner image data to determine either the general surface condition of the windshield or the surface condition found in the worst sample. A computer printer or screen is used to output the results of the analysis. In a second embodiment, the windshield scanner apparatus and method includes a digital imaging device having a two dimensional array of photo-detectors adapted to rapidly produce a set of image data containing values corresponding to the output of each of the photo-detectors. The general purpose digital computer is programmed to receive the set of image data and analyze that image data to determine the condition of the windshield surface.

In this way, the apparatus and method of the present invention provides a means for efficiently measuring surface damage over a large portion of a windshield surface. Values for surface damage can be gathered in terms of highly reflective, low transmissibility pixels per square inch for a number of sample zones and compared against a predetermined range or scale of values which represent a range from zero to that of a surface having an unacceptable degree of surface damage. Accordingly, the apparatus and method of the present invention can be employed to quickly assess the surface condition of a vehicle windshield either in a selected zone or across a large area of the windshield.

BRIEF DESCRIPTION OF THE DRAWINGS

The following detailed description refers to the attached drawings in which.

DETAILED DESCRIPTION OF THE PREFERRED EMBODIMENT

Figure 1:
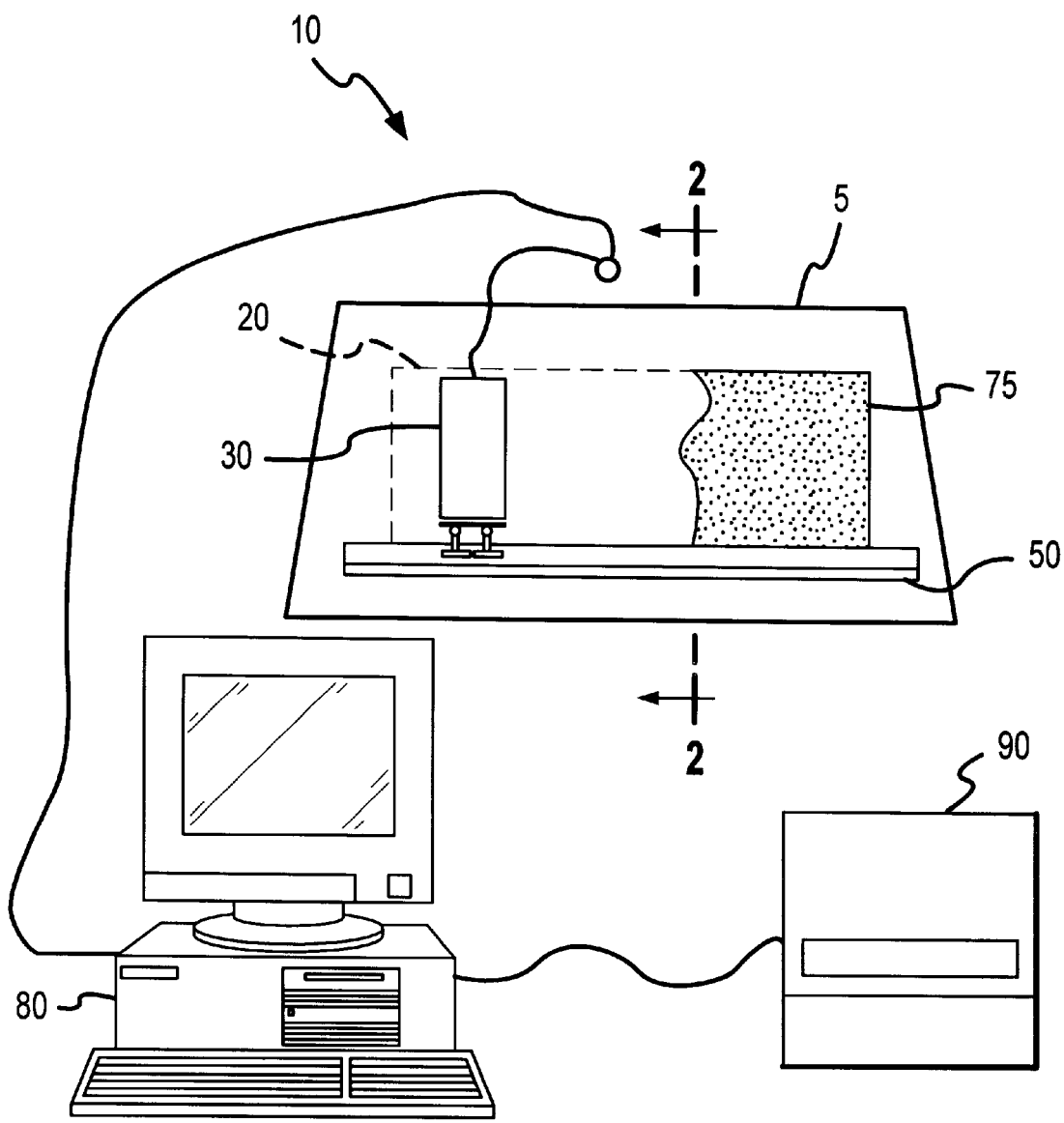
FIG. 1 is a schematic drawing of the windshield scanning system.

FIG. 1 shows a vehicle windshield scanning system 10 in relation to a vehicle windshield 5. The vehicle windshield scanning systems includes a windshield scanning apparatus 20, a general purpose digital computer 80, and a printer 90. Scanning apparatus 20 further includes a scanner assembly 30, a scanner track 50, and a black mask 75.

Figure 2:
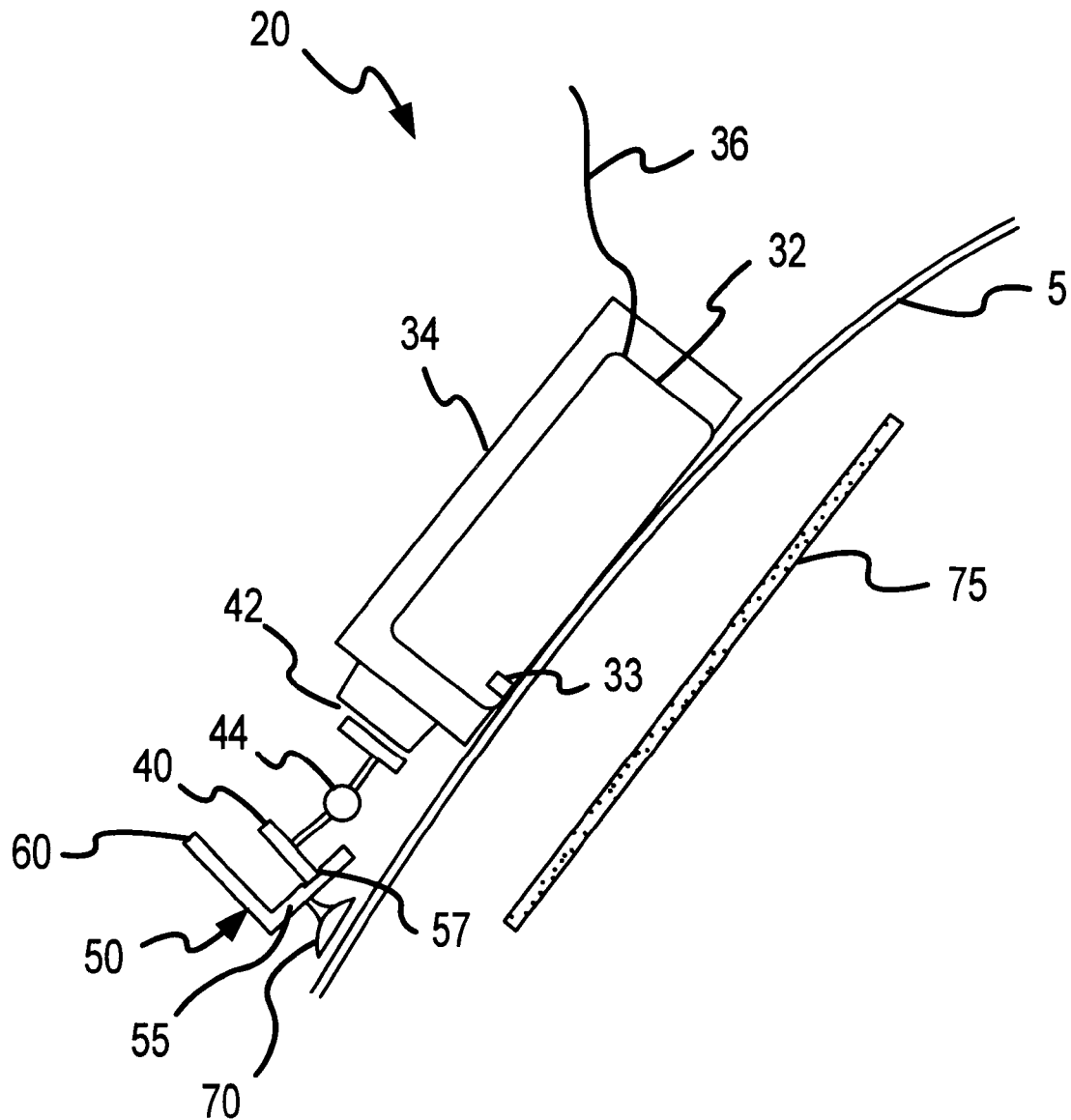
FIG. 2 is a side view of the windshield scanning apparatus taken from plane A—A of FIG. 1.

As can be seen in FIG. 2, scanner assembly 30 includes a scanner 32, a protective case 34, surrounding scanner 32 and track wheels 40. Scanner 32 can be a Logitec PageScan™ color scanner having a sight source (not shown), charge coupled device (CCD) digital photo-detectors, a drive means for driving scanner 32 across vehicle windshield 5 and a contact sensor 33. The scanner drive means propels scanner 32 and scanner assembly across the windshield surface as long as contact sensor 33 senses contact. Contact sensor 33 turns scanner 32 off if it is not in contact with windshield 5. A power and data transfer line 36 connects scanner 32 to general purpose digital computer 80. Wheels 40 are generally a pair of wheels adapted to roll in a direction parallel to the length of windshield 5 and are mounted to protective case 34 sot hat they can be adjusted at sliding joint 42 towards and away from windshield 5 and pivoted about pivot joint 44 to change their angle with respect to windshield 5.

As can be further seen in FIG. 2, scanner track 50 includes a first flange 55, a second flange 60, and suction cups 70. First flange 55 is oriented generally parallel to the windshield surface 5 while second flange 60 is continuous with and generally normal to first flange 55. Suction cups 70 are evenly spaced along the length of first flange 55 temporarily fasten scanner track 50 to windshield 5 which is adapted for receiving track wheels 40. Scanner track 50 can be made from almost any flexible material capable of conforming to the shapes of various vehicle windshields.

As can also be seen in FIG. 2, track wheels 40 ride in track wheel groove 57 of track 50. Track wheels 40 can be adjusted normally and pivotably to insure that they ride smoothly in track wheel groove 57. After scanner assembly 20 is manually placed so that flat track wheels 40 are positioned at one end of track wheel groove 57, it is activated by general purpose digital computer 80. After being activated, scanner 32 crawls across windshield 5 as track wheels 40 roll in track wheel groove 57 thereby guiding the path of scanner 32. As scanner 32 crawls across windshield 5, it shines light on windshield 5. Most of that light passes through windshield 5 without any interference, is absorbed by flat black mask 75 and is registered as black digital pixel elements by the CCD detector inside scanner 32. Scanner light which strikes a pit (not shown) in windshield 5 is scattered within the pit and is reflected back to the CCD detector within scanner 32 as one or more non-black pixel elements. The CCD detector continuously transmits image data as a series of pixel elements through power and data line 36 to general purpose digital computer 80. When track wheels 40 reach the end of track wheel groove 57, they lift in a direction away from the surface of windshield 5 thereby lifting scanner 32 from the surface of windshield 5. As scanner 32 is lifted from the surface of windshield 5, contact sensor 33 stops sensing contact and signals scanner 32 to stop. Scanner 32 then stops moving and transmitting image data to general purpose computer 80.

It should be appreciated that CCD detector within scanner 32 is a digital imaging device having a linear array of closely spaced photo-detectors. When light from a light source within scanner 32 strikes windshield 5 it passes through windshield 5 where windshield 5 is smooth. Where windshield 5 is not smooth, but pitted, the light is brightly reflected.

Because of this, the linear array of closely spaced photo-detectors within scanner 32 produces a set of discrete values where each of the values correspond to the intensity of light reflected at a discrete location on windshield 5. These discrete values having discrete locations may be called "pixels". As scanner 32 moves across windshield 5, it produces at set of discrete values corresponding to the amount of light reflected at a corresponding set of locations on the windshield surface. Discrete locations having surface damage are detected when discrete values fall into a predetermined high range indicating increased reflectivity and decreased transmissibility. A pixel having such a value falling into such a predetermined high range might be described as a "non-black" pixel. A value falling into a predetermined low range might be described as a "black" pixel. The program steps executed by the general purpose computer organize the set of discrete values so that each value is assigned a pair pixel coordinates in relation to the width of the linear array of photo-detectors in pixels and the length of scanner 32 travel in pixels so that the physical location associated with each discrete value can be known and used.

Figure 3:
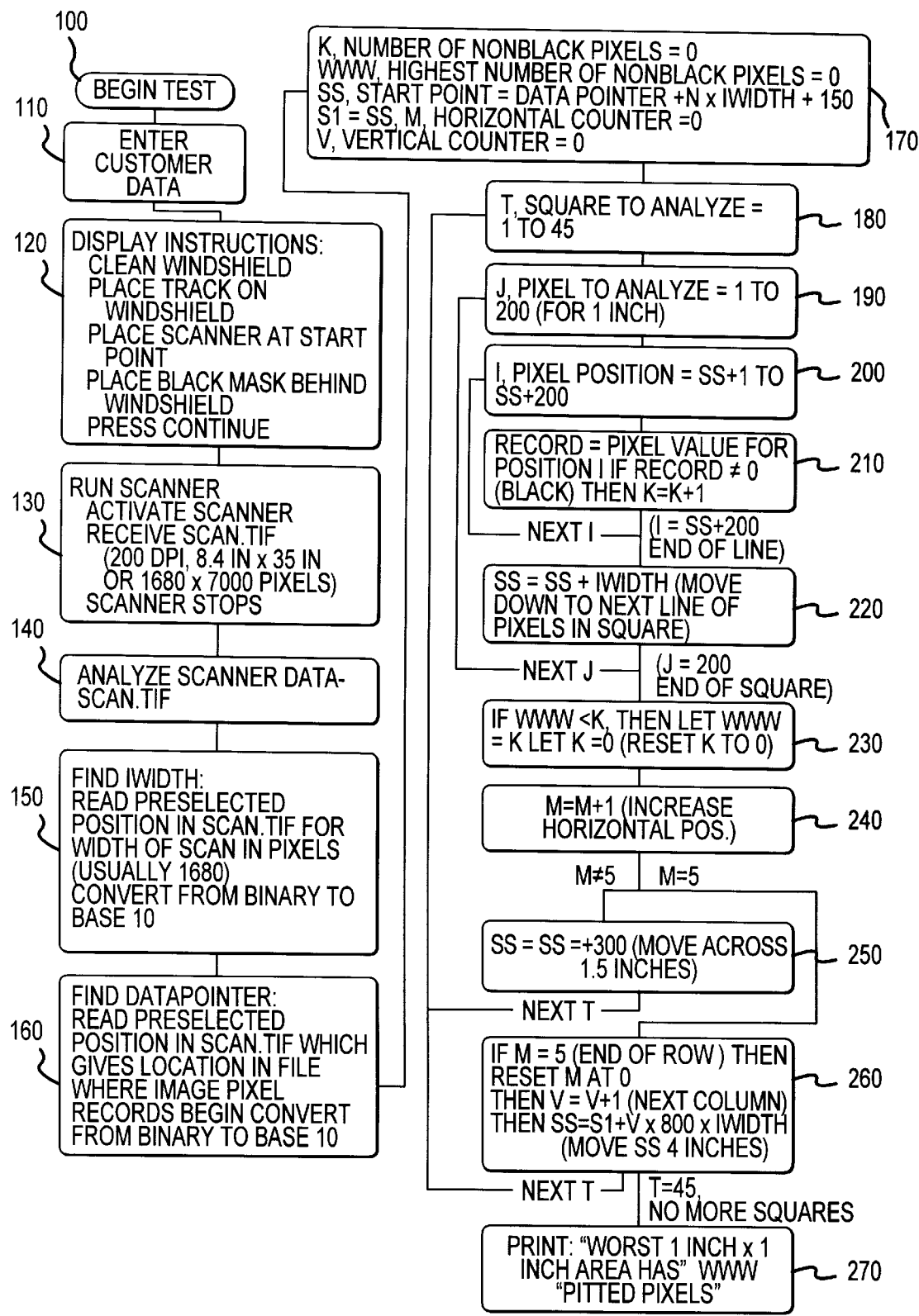
FIG. 3 is a block diagram of the analysis steps executed by the general purpose computer.

FIG. 3 is a flow chart illustrating the program steps executed by general purpose computer 80 when activating scanner 32 (see FIG. 2), receiving image data from scanner 32 and analyzing image data from scanner 32. In step 100, the 30 test is begun and in step 110 customer data such as customer name, address, make of car and number of miles on the windshield are manually entered. In step 120 instructions are displayed for setting up the windshield scanner apparatus 20. In step 130, the scanner 32 is activated and run until it is de-activated. As shown in step 130, a gray scale TIF image file is collected and given the file name SCAN.TIF. A progress bar could be displayed on the screen of general purpose computer 80 (see FIG. 1), while SCAN-.TIF is being collected.

Figure 4:
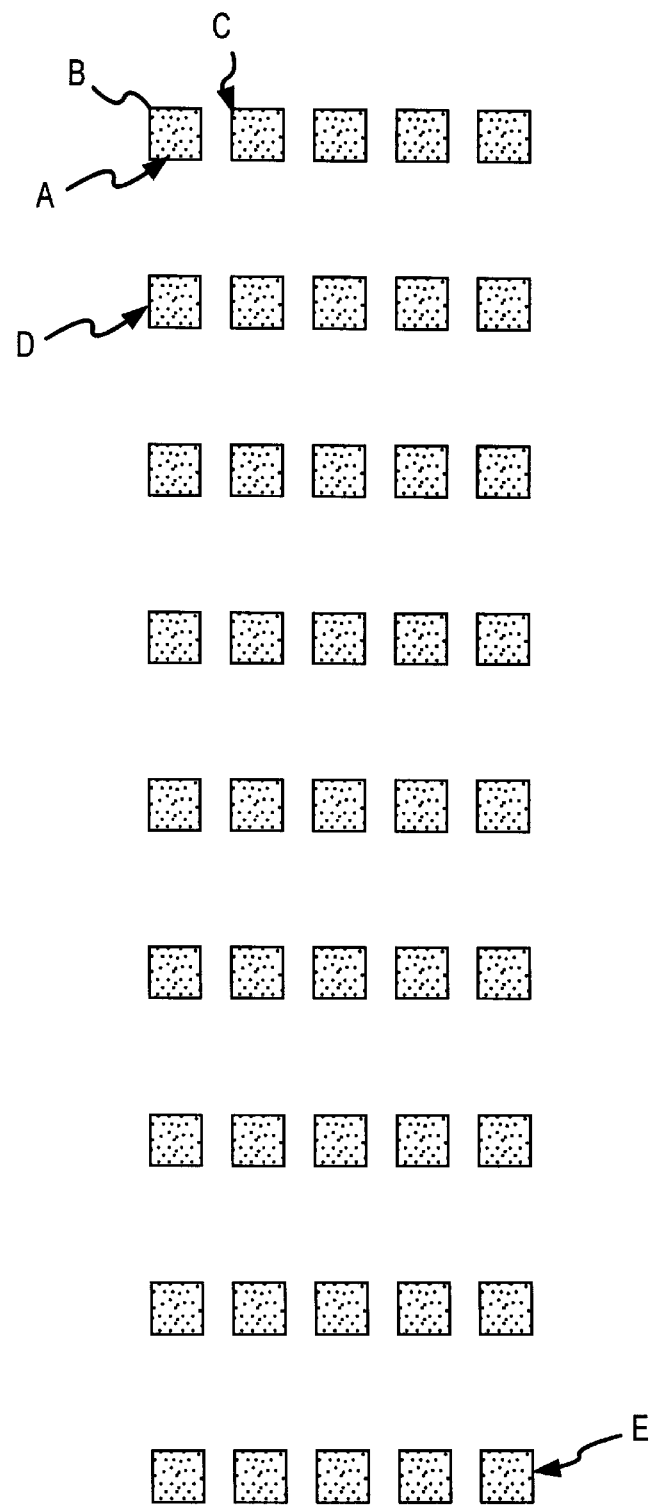
FIG. 4 is a diagram of the sample squares analyzed.

The remaining steps 140 to 280, shown in FIG. 3 are devoted to analyzing the image data collected in the form of the image file SCAN.TIF. The purpose of the method of these steps is to perform a statistically accurate analysis of the image data without analysing all of the image data. To do this discrete square zones are analysed. First, in step 150, the width of the image file is found and named "iwidth". Since scanner 32, in this example has a scan width of 8.4 inches and has a setting of 200 pixels per inch, the "iwidth" value should is 1680. In a TIF file, the file width is given at a predetermined location in the file. In step 160, datapointer, which is also at a 10 predetermined location in the TIF file gives the location in the TIF file where the pixel records begin. In step 170, k, the number of non-black pixels is set at 0, www, the highest number of non-black pixels in a square is set at 0, ss, start point is set at value equal to data pointer added to a selected number of N time "iwidth" which is further added in this example to 150 (or 0.75 inches). Turning to FIG. 4, the location in the file given by ss is in first square A at point B. Also in step 170, s1 is initially set at ss, m, the horizontal counter is set at 0, and v, the vertical counter is set at 0.

As can be seen in FIG. 3, step 180 begins a loop where t, the square number ranges from 1 to 45. In step 190, j the vertical pixel row counter ranges from 1 to 200. In step 200, i, the pixel position across a given square ranges from ss to ss+200. In step 210, k the non-black pixel counter is increased by 1 if the record in SCAN.TIF at a position corresponding to i is 0 or not black. After, step 210, if i equals ss+200, then step 230 is performed where ss is changed to a new value which corresponds to moving ahead in SCAN.TIF by "iwidth" which effectively moves i to the next line of pixels in a given square. At this point, the computer returns to step 190, adds one to j and performs steps 200 through 230 until j equals 200 at which point a given square is finished. In step 230 www, the value for the largest number of non-black pixels in a square is increased to the existing value for k if that value is larger than the old www. In step 240, m the horizontal position is increased by one. Step 250 is executed if m does not equal 5. In step 250, ss is set to a new position equivalent to moving across 1.5 inches to the staring point of a new square in the same row. Step 260 is executed if m equals 5. In step 260, m, the horizontal position is reset at 0, one is added to v as ss is reset to a position equivalent to moving down 4 inches. In step 270, the last step is executed if t, the square counter is equal to 45, or the last square. The last square is square E in FIG. 4. In step 270, www which by now is the number of non-black pixels in the square having the most non-black pixels is printed out or displayed on a screen.

It should be easily appreciated by those skilled in the art, that in step 230 above, a record could be created giving a value of k (number of non-black pixels) for each value of t (square number 1 to 45). In this way, further statistical analysis could be performed wherein the average number of non-black pixels present in all of the square sample areas, the standard deviation, the best and worst values could all be determined. It should be further appreciated by those skilled in the art that values for ss could be varied within the entire SCAN.TIF file in a random manner so that random zones of a predetermined size could be chosen to provide random sampling. The analysis method of the above example employs sample squares to significantly reduce computation time. This method, however can also be used to map out the degree of damage across the windshield surface. It should also be easily appreciated by those skilled in the art, that after a worst square has been identified, a separate image file could be extracted from SCAN.TIF in accordance with the position of the worst square and displayed so that the most pitted sample square can be visualized. It should also be appreciated that the steps of the above described method could be simplified to accomplish simple random sampling or systematic sampling of one of every ten, twenty or even one hundred records or pixels in an image file to obtain a statistically accurate assessment of windshield quality over a large surface area. The advantage of employing such a method is that an accurate assessment of a windshield could be performed with relatively simple steps in much less time.

Figure 5:
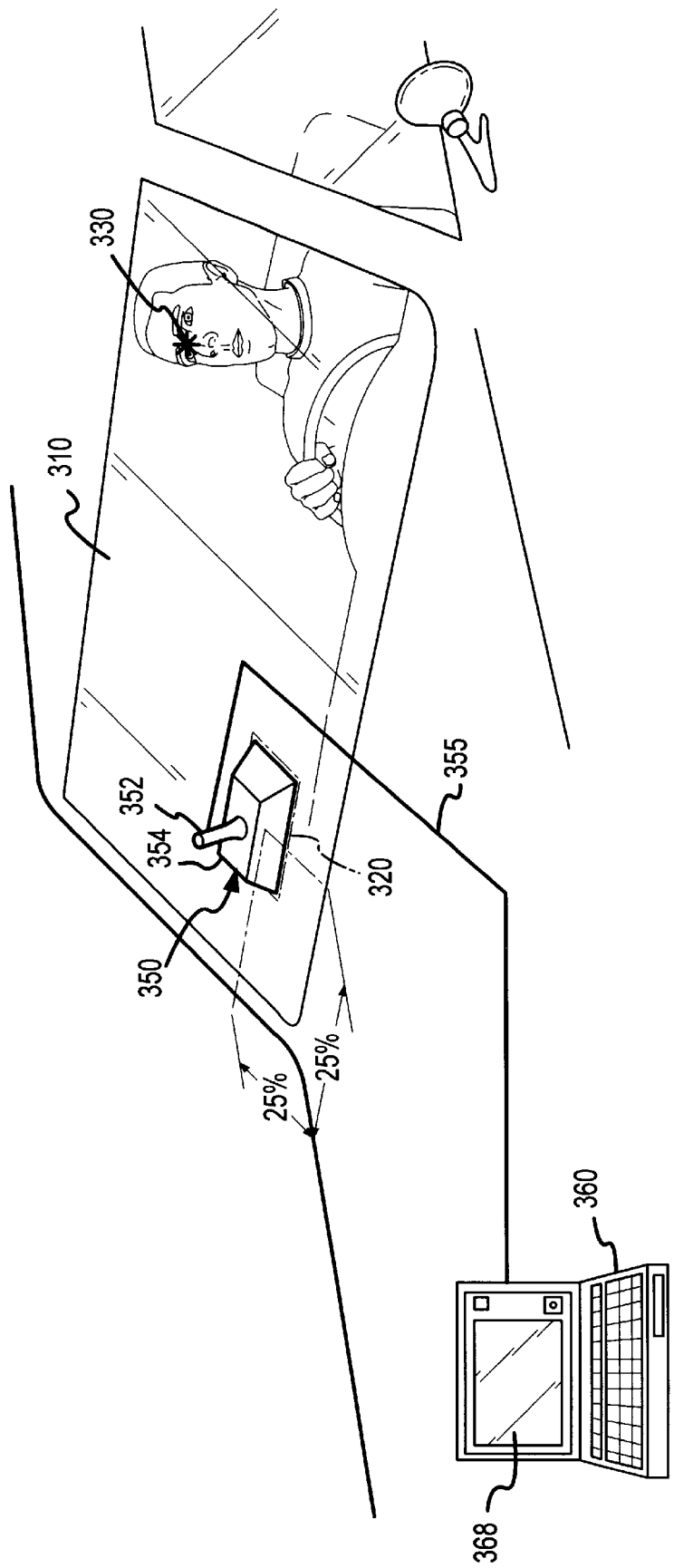
FIG. 5 is a perspective view of a peripheral glare surface damage measuring system.

FIG. 5 illustrates an alternate system measuring peripheral glare producing windshield surface damage. The inventors have discovered that windshield surface damage directly in front of the driver's eyepoint is less influential in causing vision loss due to glare than windshield surface damage in zones more distant from an operator's eyepoint. More particularly, as shown in FIG. 5, windshield 310 has a zone 320 that is located at about 25% of the windshield width and 25% of the windshield height from the corner opposite operator's eye point 330. Zone 320 of windshield 310 is the region of the windshield that produces the largest amount of scattered light producing vision loss due to glare. This is true because scattered light from zone 320 impacts more severely the peripheral light receptors of the operator's eyes than scattered light from any other region of the windshield. Consequently, a surface damage assessment from zone 320, a region that is approximately 25% up and 25% across from the far corner of the windshield opposite the operator's eye point will very quickly provide an assessment of the degree to which windshield 310 will contribute to vision loss due to glare.

FIG. 5 also shows a hand held CCD imaging device 350 which has a light source and an array of photo-detectors capable of acquiring a 200 dpi image over an area that is two by four inches. Hand held imaging device 350 also has a handle 352 and hood 354. An operator can hold imaging device 350 by handle 352 while placing hood 354 substantially flat against windshield 310 in region 320. Hand held imaging device 350 could employ a light source adapted to produce light that illuminates pits and scratches in the surface of windshield 310 while not illuminating dirt on the back of the windshield or objects inside the car. The image taken by hand held imaging device 350 could cover an area of for example two by four inches and contain 320,000 pixels. The image file having a set of values and associated pixel coordinates would be transmitted by logical communication protocol through a data transmitting means such as cable 355 as a formatted image data file to a general purpose digital computer 360. General purpose digital computer 360 receives the image file from hand held imaging device 350 and executes instructions whereby the number of non-black pixels is determined as described above and windshield surface damage is determined as a proportion of surface area that returns reflected light characteristic of pits and scratches. The results of these calculations are displayed on a screen 368 so that comparisons with new, undamaged windshields or windshields having acceptable levels of damage can be made. Using this alternate system, glare producing windshield surface damage can be very quickly measured and assessed.

The skilled reader, in view of this specification may envision numerous modifications and variations of the above disclosed preferred embodiment. Accordingly, the reader should understand that these modifications and variations, and the equivalents thereof, are within the spirit and scope of this invention and the scope of the claims.

Wherein I claim:

1. A system for measuring surface damage in a vehicle windshield surface, comprising;

a general purpose digital computer, a digital imaging device and a light source, the digital imaging device having an array of closely spaced photo-detectors, the light source shining light on the vehicle windshield surface, the digital imaging device holding the array of closely spaced photo-detectors in relation to the vehicle windshield surface whereby the array of closely spaced photo-detectors produces a set of discrete values corresponding to the intensity of the light reflecting from a set of discrete locations on the vehicle windshield surface, the set of values containing values in a predetermined high range corresponding to windshield surface locations having high reflectivity where the windshield surface has pits or scratches that reflect more light and transmit less light, the set of values also containing values in a predetermined low range corresponding to windshield surface locations having low reflectivity where the windshield surface is smooth and transmits more light and reflects less light, a means for communicating the set of values from the digital imaging device to the general purpose digital computer, the general purpose digital computer programmed with a set of instructions for receiving the set of discrete values from the digital imaging device, counting the total number of discrete values, counting the number of discrete values in the predetermined high range and displaying the number of discrete values in the predetermined high range in relation to the total number of discrete values, the proportion of the vehicle windshield surface having surface damage is measured and displayed.

2. The system for measuring surface damage in a vehicle windshield surface of claim 1 further comprising;

a general purpose digital computer programmed with a set of instructions having steps for sampling a sub set of the total number of discrete values, counting the number of discrete values in the predetermined high range and displaying the number of discrete values in the predetermined high range in relation to the total number of discrete values sampled, whereby a statistically accurate assessment of the proportion of the vehicle windshield surface having surface damage is measured and displayed very rapidly.

3. The system for measuring surface damage in a vehicle windshield surface of claim 1 wherein, the digital imaging device comprises a two dimensional array of photo-detectors and the digital imaging device is adapted to record an image from a zone on the surface of the windshield.

4. The system for measuring surface damage in a vehicle windshield surface of claim 1 wherein, the windshield includes a projected eyepoint corresponding the center position of a vehicle operator's eyes projected on to the windshield, the digital imaging device comprises a two dimensional array of photo-detectors adapted to record an image from a zone on the surface of the windshield and the digital imaging device is located in the opposite corner of the windshield from the projected eyepoint at approximately 25% of the windshield width and 25% of the windshield height from the corner opposite the operator's eyepoint, whereby the digital imaging device and the general purpose digital computer record and measure glare producing surface damage in a zone on the windshield most likely to cause vision loss due to glare.

5. The system for measuring surface damage in a vehicle windshield surface of claim 1 wherein the light source is a polarized light source to reduce the tendency of the light to reflect from a smooth surface.

6. A system for measuring surface damage in a vehicle windshield surface, comprising;

a general purpose digital computer, a digital scanner, a scanner track, the scanner track disposed horizontally across the vehicle windshield, the scanner track adapted for receiving and guiding a pair of wheels, the digital scanner having a linear array of closely spaced photo-detectors, a light source and guide wheels adapted to roll along the scanner track, the digital scanner adapted to crawl across the vehicle windshield surface while the guide wheels roll along the scanner track and guide the path of the scanner, the light source of the digital scanner shining light on the vehicle windshield surface as the digital scanner crawls across the vehicle windshield surface, the closely spaced photo-detectors of the digital scanner adapted to produce a set of discrete values as the scanner crawls across the vehicle windshield surface, the discrete values corresponding to the intensity of the light reflecting from a set of discrete locations on the vehicle windshield surface, the set of values containing values in a predetermined high range corresponding to windshield surface locations having high reflectivity where the windshield surface has pits or scratches that reflect more light and transmit less light, the set of values also containing values in a predetermined low range corresponding to windshield surface locations having low reflectivity where the windshield surface is smooth and transmits more light and reflects less light, a means for communicating the set of values from the digital scanner to the general purpose digital computer, the general purpose digital computer programmed with a set of instructions for activating the operation of the digital scanner and for receiving the set of discrete values from the digital scanner, counting the total number of discrete values, counting the number of discrete values in the predetermined high range, and displaying the number of discrete values in the predetermined high range in relation to the total number of discrete values, the proportion of the vehicle windshield surface having surface damage is measured and displayed.

7. The system for measuring surface damage in a vehicle windshield surface of claim 6 further comprising;

a general purpose digital computer programmed with a set of instructions having steps for sampling a sub set of the total number of discrete values, counting the number of discrete values in the predetermined high range and displaying the number of discrete values in the predetermined high range in relation to the total number of discrete values sampled, whereby a statistically accurate assessment of the proportion of the vehicle windshield surface having surface damage is measured and displayed very rapidly.

8. The system for measuring surface damage in a vehicle windshield surface of claim 6 further comprising;

a general purpose digital computer programmed with a set of instructions for receiving the set of discrete values from the digital scanner as a formatted set of data having a predetermined width in pixels and a recorded length in pixels, each of the discrete values in the formatted set of data is also associated with a pair of coordinates corresponding to a width position and a length position, the set of instructions also including steps adapted to isolate values within a set of zones, the zones within a pattern of zones where each zone contains values within ranges of width positions and length positions, the set of instructions having steps to count and display the number of discrete values in the predetermined high range in each zone in relation to the total number of discrete values in each zone.

9. The system for measuring surface damage in a vehicle windshield surface of claim 6 wherein the light source is a polarized light source to reduce the tendency of the light to reflect from a smooth surface.

10. A method for measuring surface damage in a vehicle windshield surface, comprising the steps of;

placing a digital imaging device having an array of closely spaced photo-detectors and a light source in closely spaced relation to a vehicle windshield surface, using a general purpose digital computer to execute program instructions that; activates the digital imaging device, the digital image device producing a set of discrete values corresponding to the intensity of the light reflecting from a set of discrete locations on the vehicle windshield surface, the set of values containing values in a predetermined high range corresponding to windshield surface locations having high reflectivity where the windshield surface has pits or scratches that reflect more light and transmit less light, the set of values also containing values in a predetermined low range corresponding to windshield surface locations having low reflectivity where the windshield surface is smooth and transmits more light and reflects less light, transmitting the set of values from the digital imaging device to the general purpose digital computer, the general purpose digital computer executing a set of instructions to receive the set of discrete values from the digital imaging device, count the total number of discrete values, count the number of discrete values in the predetermined high range corresponding to discrete locations having a damaged surface condition with high reflectivity and low transmissibility and displaying the number of discrete values in the predetermined high range in relation to the total number of discrete values, the proportion of the vehicle windshield surface having surface damage is measured and displayed.

11. The method for measuring surface damage in a vehicle windshield surface of claim 10, wherein;

the digital imaging device has an linear array of closely spaced photo-detectors defining a linear array of pixels and the digital imaging device further includes a drive means for driving the digital imaging device across the windshield surface, and wherein the general purpose digital computer also executes instructions to obtain from the imaging device a two dimensional array of discrete values each having associated pairs of coordinates in relation to the width in pixels of the digital imaging device and the length in pixels in relation to the length of travel of the digital imaging device.

12. The method for measuring surface damage in a vehicle windshield surface of claim 10, wherein;

the digital imaging device has an linear array of closely spaced photo-detectors defining a linear array of pixels and the digital imaging device further includes a drive means for driving the digital imaging device across the windshield surface, wherein the general purpose digital computer also executes instructions to obtain from the imaging device a two dimensional array of discrete values each having associated pairs of position coordinates in relation to the width in pixels of the digital imaging device and the length in pixels in relation to the length of travel of the scanner, and wherein, the general purpose digital computer also executes instructions to determine at least one zone of pixels using their position coordinates, count the number of discrete values in the at least one zone, count the number of discrete values in the predetermined high range corresponding to discrete locations having a damage surface condition with high reflectivity and low transmissibility in the at least one zone, and display the number of discrete values in the predetermined high range in relation to the total number of discrete values in the at least one zone, whereby the proportion of the vehicle windshield surface having surface damage in the at least one zone is measured and displayed.

* * * * *